United States Patent [19]

Pronovost et al.

[11] Patent Number: 5,132,205

[45] Date of Patent: Jul. 21, 1992

[54] HIGH PH EXTRACTION COMPOSITION AND ITS USE TO DETERMINE A CHLAMYDIAL, GONOCOCCAL OR HERPES ANTIGEN

[75] Inventors: Allan D. Pronovost, San Diego, Calif.; John C. Mauck, Rochester; Sheryl S. Sullivan, Hilton, both of N.Y.; Catherine E. Greer; James H. Gilbert, both of Oakland, Calif.

[73] Assignee: Eastman Kodak Company, Rochester, N.Y.

[21] Appl. No.: 255,928

[22] Filed: Oct. 7, 1988

[51] Int. Cl.$^5$ ............ C12Q 1/70; C12Q 1/02
[52] U.S. Cl. .................... 435/5; 435/7.21; 435/7.36; 435/871; 435/4 CM; 436/825
[58] Field of Search ............ 435/4, 5, 7, 292; 436/510, 511, 543, 17, 163, 825, 826; 530/305, 344, 806, 820, 825, 826

[56] References Cited

U.S. PATENT DOCUMENTS

| | | |
|---|---|---|
| 4,245,038 | 1/1981 | Weetall . |
| 4,427,782 | 1/1984 | Caldwell et al. . |
| 4,497,899 | 2/1985 | Armstrong et al. . |
| 4,497,900 | 2/1985 | Abram et al. ............ 436/511 |
| 4,663,291 | 5/1987 | Rose . |
| 4,828,978 | 5/1989 | Warren et al. ............ 435/36 |

FOREIGN PATENT DOCUMENTS

| | | |
|---|---|---|
| 0174106 | 8/1985 | European Pat. Off. . |
| 174106 | 8/1985 | European Pat. Off. . |
| 183383 | 10/1985 | European Pat. Off. . |
| 193431 | 1/1986 | European Pat. Off. . |
| 264036 | 10/1987 | European Pat. Off. . |

OTHER PUBLICATIONS

Caldwell et al., *J. Clin. Microbiol.*, 18(3); pp. 539–545 (1983).

Schmeer et al., *J. Clin. Microbiol.*, 15(5), pp. 830–834 (1982).

Terho et al., *J. Immuno.*, 2(3&4), pp. 239–262 (1981).

*Primary Examiner*—Sam Rosen
*Attorney, Agent, or Firm*—J. Lanny Tucker

[57] ABSTRACT

An extraction composition is useful for lysing chlamydial, gonococcal or herpes organisms and extracting detectable antigen from the organisms. In particular, this composition has a high pH (at least about 8) and comprises an alcoholamine which is effective in extracting antigen. It is particularly useful for extracting either or both of the lipopolysaccharide and major outer membrane protein chlamydial antigens.

10 Claims, No Drawings

HIGH PH EXTRACTION COMPOSITION AND ITS USE TO DETERMINE A CHLAMYDIAL, GONOCOCCAL OR HERPES ANTIGEN

FIELD OF THE INVENTION

This invention relates to an extraction composition and its use in the determination of chlamydial, gonococcal or herpes organisms. In particular, it relates to a composition useful for the extraction of the appropriate antigen, a method of extraction and a method of determining the antigen.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is *Chlamydia trachomatis* (herein *C. trachomatis*) which is one of two microbial species of the genus Chlamydiaceae, order Chlamydiales. There are 15 or more strains of this species which are the causes of a number of human ocular and genital diseases including trachoma, inclusion conjunctivitis, lymphogranuloma venereum, nongonococcal urethritis and proctitis. Infection from *C. trachomatis* is pervasive in the general population so that it is believed that there are millions of cases each year of nongonococcal urethritis alone.

Despite the increasing control of various viruses by vaccination and various anti-viral agents, infection by organisms such as herpes simplex virus (HSV) remains a serious problem. There are two types of HSV, type 1 which occurs mainly around the mouth while type 2 occurs primarily around the genital area of the human body. Skin infections and viral encephalitis are but two of the serious results from HSV infection.

Gonorrhea is a disease usually transmitted by sexual contact caused by a bacterium of the Neisseria genus, especially *N. gonorrhoeae*. The disease has plagued mankind for thousands of years, and although antibiotics have helped control its spread, it still persists in epidemic proportions in many parts of the world. The importance of detection and treatment of this organism is well recognized. *N. meningitidis* and *N. lactamica* are also species of considerable medical and diagnostic interest.

Because of the widespread nature of these diseases, there is considerable interest in having a rapid, simple and reliable test for detection of the causative organisms. Considerable research has been carried out to find useful ways to extract detectable antigen from the organism. See for example, U.S. Pat. Nos. 4,427,782 (issued Jan. 24, 1984 to Caldwell et al) and 4,663,291 (issued May 5, 1987 to Rose) and E.P. Publications 174,106 (Becton) and 193,431 (Caldwell et al) which described extraction techniques for chlamydial antigens in particular.

Extraction of antigen from the organisms in a biological specimen is critical to providing an accurate, rapid and sensitive assay. Many varied techniques have been used for extraction including physical disruption of the cells by sonication, heating or centrifugation. Chemical extraction compositions have also been developed. For example, the lipopolysaccharide antigen of chlamydial organisms has been extracted using a mixture of phenol and water in E.P. Publication 193,431 (noted above).

Ethanolamine has been used in combination with surfactants and high temperature heating (for example, 70°-110° C.) to extract chlamydial antigens at a pH below 8 as described in E.P. Publication 183,383 (IQ BIO).

High pH extraction is described in E.P. Publication 174,106 (noted above) wherein a test specimen is subjected to pH 6 to 8, followed by subjection to pH 8 to 12.5 and subsequent neutralization. During the high pH step, the specimen is subjected to 5-30 minutes of incubation, some of which time is at high temperature (up to 100° C.).

Assays for *C. trachomatis* and *N. gonorrhoeae* carried out using a solid support are described in U.S. Pat. Nos. 4,497,899 and 4,497,900 (issued Feb. 5, 1985 to Armstrong et al and Abram et al, respectively). The described assays are performed by extracting antigen from the organism using a combination of an anionic or nonionic surfactant, deoxycholate and dithiothreitol, and coating it on a bare solid support. The coated antigen is then detected with either one or two antibodies, one of which is suitably labeled. Attachment of antigen is apparently achieved by incubating the coated support for an extended time sufficient to cause adsorption of antigen thereon (Col. 2, lines 51-55). From the examples of the first patent, this time is determined to be at least 30 minutes at elevated temperature (37° C.). The entire assay described in U.S. Pat. No. 4,497,899 takes at least 3 hours to perform.

It would be desirable to have much more rapid tests for chlamydial, gonococcal and herpes antigens which have high reliability and can be performed at room temperature. Such tests would be highly dependant upon a simple, rapid and effective extraction composition and procedure which does not require high temperatures or long incubation periods.

SUMMARY OF THE INVENTION

The problems noted above are overcome with an extraction composition useful for extracting antigen from chlamydial, gonococcal or herpes organisms, the composition having a pH of at least about 8 and comprising a strong base and an alcoholamine present in an amount of at least about 1 mg/ml.

This invention also provides a method for extracting antigen from chlamydial, gonococcal or herpes organisms comprising:

A. providing a specimen suspected of containing chlamydial, gonococcal or herpes organisms, and B. contacting the specimen with the extraction composition described above to extract chlamydial, gonococcal or herpes antigen, respectively, for detection.

A method for the determination of a chlamydial, gonococcal or herpes antigen comprises:

A. extracting chlamydial, gonococcal or herpes antigen from a specimen suspected of containing chlamydial, gonococcal or herpes organisms, respectively, with the extraction composition described above, B. contacting the extracted antigen with antibodies thereto to form an immunological complex, and C. determining the presence of the complex as an indication of the presence of the organisms in the specimen.

The extraction composition of this invention rapidly and effectively lyses chlamydial, gonococcal or herpes organisms in a biological specimen to release sufficient antigen for a sensitive assay. Lysis can be carried out very quickly, usually in less than 10 minutes, and at room temperature using standard equipment. The operator skills required are not unusual, and high temperature extraction is avoided. Both lipopolysaccharide and major outer membrane protein antigens are extracted for chlamydial assays, although the lipopolysaccharide is of primary interest. Gonococcal assays involve the extraction of a principle outer membrane protein, such as protein IA or IB, while herpes assays involve the extraction of membrane glycoproteins.

These advantages are achieved because of the use of an extraction composition which has a high pH and includes an alcoholamine or salt thereof in an amount of at least about 1 mg/ml. The composition pH is at least about 8, and preferably at least about 9.

DETAILED DESCRIPTION OF THE INVENTION

The present invention includes an extraction composition and method, as well as a method for determining the presence of chlamydial, gonococcal or herpes organisms in a biological specimen which has been obtained from a patient using standard medical and microbiological techniques. Such specimens include, for example, swab specimens obtained from the cervix, urethra, eyes, throat or anus of a patient, and body fluids such as synovial fluid or fluid from lesions. The biological specimens so obtained are suspected of containing chlamydial, gonococcal or herpes organisms which comprise the antigens to be determined.

While some assays in the art are designed to detect whole bacterial or virus infected cells, it is an advantage of this invention that the bacterial cells or viruses are effectively lysed and sufficient antigen extracted from the cellular matter to provide a sensitive assay in a relatively short period of time. Antigens are either extracted from infected whole host cells or from reticulate or elementary bodies present in the sample.

The chlamydial antigens generally detected according to the present invention are the lipopolysaccharide (glycolipid group) antigen of the organism as described, for example, in E.P. Publication 193,431 (noted above), or the major outer membrane protein of the organism as described in U.S. Pat. No. 4,427,782 (noted above). In one embodiment, both antigens are detected simultaneously. However, the lipopolysaccharide is of most interest in the practice of a preferred embodiment to detect *C. trachomatis.*

In other embodiments, various gonococcal organisms, such as *N. gonorrhoeae,* are detected by determining the presence of extracted protein IA or IB outer membrane antigens from the organisms. A single strain may be detected, or preferably, a mixture of strains is detected.

Still other embodiments represent the detection of HSV strains, either HSV-I or HSV-2 alone or both together. Glycoproteins of the virions are extracted and detected with the present invention. In addition, virus infected cells can be lysed and solubilized to release intracellular viruses or membrane associated viral antigens.

The extraction composition of this invention has a pH of at least about 8, and preferably of at least about 9, using any suitable buffer, strong base or mixture thereof. A pH of at least 10 is most preferred. Generally, the appropriate pH is provided by including appropriate amounts of a strong base or buffer in the composition. As used herein, the term "strong base" is intended to mean a compound which has a pKa of at least about 8 at 25° C. Preferred strong bases have a pKa of at least about 9 at 25° C. Useful bases would be readily apparent to one skilled in the art, but include alkali metal, alkaline earth and ammonium hydroxides (such as sodium hydroxide, potassium hydroxide, calcium hydroxide, ammonium hydroxide and lithium hydroxide), phosphates (such as trisodium phosphate, and tripotassium phosphate), tri(hydroxymethyl)aminomethane and similar compounds. The amount of strong base in the composition would vary depending upon the pKa of the base, but generally from about 1 to about 30 mg/ml is useful, and from about 2 to about 20 mg/ml is preferred.

The extraction composition further comprises an alcoholamine or salt thereof in an amount of from about 1, and preferably from about 2 to about 30, mg/ml. Useful alcoholamines include ethanolamine, diethanolamine, propanolamine, triethanolamine and salts thereof. Others would be readily apparent to one skilled in the art.

Other addenda are preferably included in the extraction composition, including a cationic surfactant (especially when extraction of the major outer membrane protein is desired), one or more reducing agents, preservatives to prevent hydrogen peroxide activity, chelating agents and anti-foaming agents.

Preferably, at least about 1, and more preferably from about 2 to about 10, mg/ml of one or more cationic surfactants are present. Such compounds are positive in charge. Each compound may also have negative charges as long as the net compound charge is positive. The positive charges can be provided by quaternary ammonium salts, quaternary phosphonium salts, quaternary sulfonium salts, quaternary pyridinium salts or others known in the art. Preferably, the charges are provided by quaternary ammonium groups. Particularly useful cationic surfactants are described in more detail in copending and commonly assigned U.S. Ser. No. 255,926 filed on even date herewith by Mauck and Green and entitled "Use of a Cationic Surfactant to Extract the Chlamydial Major Outer Membrane Protein Antigen", incorporated herein by reference.

The extraction composition of this invention can also contain a suitable amount of reducing agent, such as dithiothreitol, cysteine and β-mercapto-ethanol. Dithiothreitol is preferred. The reducing agent is generally present in an amount of at least about 5 mmolar, and preferably from about 20 to about 50, mmolar. Further details are provided in copending and commonly assigned U.S. Ser. No. 255,921 filed on even data herewith by Mauck and Zercie and entitled "Stabilized Extraction Composition Having a Sulfhydryl-Containing Reducing Agent and Its Use in Chlamydial and Gonococcal Determinations", incorporated herein by reference.

When the test specimen contains whole blood or mucus, the extraction composition of this invention is desirably used with one or more proteases (described below). Proteases are a group of enzymes which hydrolyze the peptide bonds of proteins and form smaller peptides. They can be obtained from various sources, including microorganisms, such as bacteria and fungi, animal or human organs (for example the pancreas) plants (such as papaya) and others known in the art. Proteases can also be obtained from genetically altered microorganisms. Many proteases are commercially available (for example from Sigma Chemical Co.). Further details about proteases are provided in copending and commonly assigned U.S. Ser. No. 255,922 filed on even date herewith by Gilbert, Mauck and Stowers and entitled "Use of a Protease in the Extraction of Chlamydial, Gonococcal and Herpes Antigens", incorporated herein by reference.

Extraction can be carried out by providing a biological specimen suspected of containing chlamydial, gonococcal or herpes organisms and contacting it with the extraction composition of this invention in a suitable container for enough time to lyse the cells and extract antigen for assay. Generally, the extraction procedure takes less than 10 minutes although a longer time may be desired with certain specimens. Contact is generally carried out at room temperature (that is, from 18° to 25° C.), but higher temperatures up to about 40° C. may be used if desired. However, the higher temperatures required in the art can be avoided by practicing this invention. Agitation of the specimen may be desirable. Preferably, extraction is carried out in a suitable extraction device which may be designed specially for that purpose. A number of such devices are known in the art, such as U.S. Pat. No. 4,746,614 (issued May 24, 1988 to Devaney, Jr. et al).

After suitable incubation, the solution containing extracted antigen can be neutralized with a suitable acid to reduce the pH to between 6 and 8, if desired. It may also be treated to remove endogenous peroxides. Once the antigen is extracted from the organisms, it is desirable, although not essential, that the noted solution be prefiltered to remove cellular debris, particulate matter and other unwanted materials prior to further handling. Prefiltering can be carried out in a suitable container having a filter of some type.

The filtered specimen is then subjected to any of a number of analytical procedures in order to determine the presence of extracted antigen. Such procedures include culture techniques, counter-immunoelecphoresis and serological tests which, while not preferred, may be the only choice in certain instances.

Preferably, the extracted antigen is detected using an immunoassay in which it is immunologically reacted with one or more appropriate antibodies. The resulting immunological complex is detected using a suitable radiometric, colorimetric, fluorometric or enzyme labeled reagent. In some cases, the reagent is a labeled antibody to the antigen, and in other cases, the labeled anti-antibody is directed to an unlabeled antibody which is reactive with the antigen. Such immunoassays generally include the formation of a detectable immunological complex on a solid support of some type, either coated or uncoated, followed by appropriate detection procedures. Other assays involve agglutination of the immunological complex when at least one reactant (such as an antibody) of the complex is attached to labeled or unlabeled particles of some type that clump together during complex formation.

Examples of useful assays include competitive immunoassays or enzyme-linked immunoabsorbent assays (or what is commonly called "ELISA"). Such assays are described generally in U.S. Pat. No. 4,427,782 (noted above) and by Schmeer et al, *J. Clin. Microbiol.*, 15(5), pp. 830–834 (1982). The chlamydial, gonococcal or herpes antibodies used can be directed to either or several antigens being extracted from the organisms. In one embodiment, antibodies are directed to a single antigen, such as the lipopolysaccharide of the *C. trachomatis*. In other embodiments, a mixture of different antibodies is directed to several antigens, such as those extracted from several gonococcal strains.

A similar solid phase immunoassay is described in U.S. Pat. Nos. 4,497,899 and 4,497,900 (both noted above) in which extracted antigen is adsorbed to an uncoated support by incubation at elevated temperatures over a lengthy time.

A preferred immunoassay is described and claimed in copending and commonly assigned U.S. Ser. No. 255,923 filed on even date herewith by Pronovost and entitled "Determination of a Chlamydial or Gonococcal Antigen Using A Positively-Charged Ionically Binding Support". Generally, this assay is described as follows while further details can be obtained by consulting the noted application. The extracted antigen is contacted with a polymeric solid support which has a multiplicity of positively charged groups on the surface thereof. This support can be constructed of any natural or synthetic polymeric material with suitable cationic groups thereon which will ionically bind to the extracted antigen. Useful charged polymers include polyesters, polyamides, polycarbonates, polyethyleneimines, cellulosic materials and addition polymers prepared from ethylenically unsaturated vinyl monomers and others known in the art having the requisite charged groups. Generally, the cationic groups are quaternary ammonium salts, quaternary phosphonium salts, quaternary sulfonium salts, quaternary pyridinium salts, quaternary pyrimidinium salts or quaternary imidazolium salts, with quaternary ammonium salts being preferred.

The polymeric support (coated or uncoated) can be configured in any suitable form, such as beads, gels, films or membranes. It can be coated with a surfactant which may enhance assay performance. A microporous membrane is preferred as described below.

The support described herein can be used in combination with other equipment (bottles, test tubes, swabs, beakers or cups) in order carry out the assay. Alternatively and preferably, the support is a microporous membrane which is fitted into a disposable test device in which the assay can be carried out and all fluids accommodated. Useful configurations of test devices are known in the art including U.S. Pat. Nos. 3,825,410 (issued Jul. 23, 1974 to Bagshawe), 3,888,629 (issued Jun. 10, 1975 to Bagshawe), 3,970,429 (issued Jul. 20, 1976 to Updike) and 4,446,232 (issued May, 1984 to Liotta). Particularly useful devices are described and claimed in copending and commonly assigned U.S. Ser. Nos. 19,810 (filed Feb. 27, 1987 by Hinckley) and 98,248 (filed Sep. 18, 1987 by Hinckley).

Almost immediately upon contact of the antigen with the surfactant-coated or ionically charged support, the antigen is bound directly to the support. By "directly" is meant that the antigen is not bound through a linking biological compound (such as an antibody) which is attached to the support.

Therefore, within about 10 minutes, and preferably within 1 to 5 minutes, of the contact, the bound antigen is contacted with suitable antibody (either directed to a chlamydial, gonococcal or herpes antigen) so as to form an immunological complex on the support. If the assay is carried out using a disposable test device, the support can be a microporous membrane through which fluid and uncomplexed materials in the specimen are allowed to flow through as the antigen is bound to the membrane.

The antibodies used in this assay can be polyclonal or monoclonal which can be purchased or prepared using known procedures.

In one embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent compounds, chemiluminescent compounds, phosphorescent compounds, biotin or its derivatives, avidin or its derivative, ferritin, magnetizable particles, dyed particles and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates and dye-providing reagents are also needed.

In a particularly preferred embodiment, the label is peroxidase, and at some point in the assay, hydrogen peroxide and suitable dye-forming reagents are added to provide a detectable dye. For example, useful dye-providing reagents include tetramethylbenzidine and derivatives thereof, and leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide (that is, compounds which react to provide a dye upon catalytic action of peroxidase).

In a most preferred embodiment, the chlamydial, gonococcal or herpes antibody is not labeled, and detection of the antibody-antigen complex formed and bound to the support is accomplished using a second antibody (described below) which is specific to the chlamydial, gonococcal or herpes antibody, respectively, and appropriately labeled.

The antigen-antibody complex can be formed in the presence of one or more blocking proteins which reduce nonspecific interactions on the support. Useful proteins are well known and include, for example, casein, α-casein, fetal bovine serum and porcine gamma globulin. A particularly useful blocking composition comprises a nonimmunological protein and an amphoteric surfactant, as described and claimed in copending and commonly assigned U.S. Ser. No. 255,925 filed on even date herewith by Pronovost and entitled "Immunological Reagent Composition and Its Use in the Determination of Chlamydial or Gonococcal Antigens."

To hasten the formation of the immunological complex bound to the support, the antibody and antigen are generally incubated at a temperature of from about 15° to about 30° C. for up to 10 minutes. Preferably, the incubation is at room temperature (i.e. from 18° to 25° C.) for up to 5 minutes.

After the incubation and within about 10 minutes of the antibody-antigen contact, the bound complex is washed one or more times with a buffered wash solution which generally has a pH of from about 7 to about 11. The solution preferably contains one or more surfactants to aid in separating uncomplexed materials from the complex on the support. Particularly useful surfactants are cationic surfactants. Preferred wash solutions are the subject of copending and commonly assigned U.S. Ser. No. 255,924, filed on even date herewith by Pronovost and Gilbert and entitled "Wash Solution Containing a Cationic Surfactant and Its Use in Chlamydial and Gonococcal Determinations."

In the embodiment described above where the chlamydial, gonococcal or herpes antibody is labeled, the assay procedure after washing is to detect the label directly or indirectly after addition of the appropriate reagents. This is done relatively quickly after washing the bound complex. If desired, label detection can be hastened with incubation if the reagents warrant it. The label is then detected using standard equipment and procedures.

In the preferred embodiment, the chlamydial, gonococcal or herpes antibody is unlabeled, and after washing the bound complex, it is contacted with an antibody directed to the that unlabeled antibody. This second antibody (that is an anti-antibody) is appropriately labeled with any of the labels described above. The antibody can be monoclonal or polyclonal and either purchased or prepared using known techniques.

After this contact, the resulting antigen-antibody-antibody complex which is bound to the support is incubated for up to about 10 minutes at a temperature of from about 15° to about 30° C. Preferably, the incubation is at room temperature for up to about 5 minutes.

Further washing is carried out to remove uncomplexed materials, and suitable enzyme substrates or other needed reagents are added to provide a detectable species. The bound antigen-antibody-labeled antibody complex is then detected on the support using standard radiometric, colorimetric, fluorescent or other detection techniques.

The following examples are provided to illustrate, but not limit the scope of, the present invention.

Antigen Preparation

Serovar H antigen purified elementary bodies were obtained from Professor W. J. Newhall of Indiana University. Stock antigen solution (5 μl, containing 3240 ng antigen/μl) was added to a solution (50 μl) of bovine serum albumin in phosphate buffered saline (0.1 mg/ml) and stored at −80° C. to obtain solution A. This solution was thawed and mixed by vortexing and sonicating, followed by mixing 15 μl with the bovine serum albumin solution (945 μl) by vortexing to obtain solution B, the antigen concentration being $4.6 \times 10^5$ pg/100 μl. Solution B (100 μl) was then mixed with bovine serum albumin in phosphate buffered saline (900 μl) to obtain solution C having an antigen concentration of $4.6 \times 10^4$ pg/100 μl.

Antibody Preparations

The mouse monoclonal antibody to the chlamydial lipopolysaccharide (LPS) antigen was prepared using standard hybridoma technology and mouse cell line and stored in a solution of phosphate buffered saline solution (pH 7.4), containing 0.01 weight % azide as a preservative. An antibody solution was prepared by adding a sample (19 μl) of the antibody solution to a phosphate buffered saline solution (diluting 1:800) containing casein (0.5 weight %) as a blocking protein and Lonzaine ® C. amphoteric surfactant (0.01 weight %), available from Lonza Company), then filtered through a 0.22 μmeter filter to obtain a working solution.

The mouse monoclonal antibody to the chlamydial major outer membrane protein (MOMP) antigen was prepared using standard hybridoma technology and a mouse cell line and stored in a solution of phosphate buffered saline solution (pH 7.4) containing 0.01 weight % azide. An antibody solution was prepared by adding a sample (14 μl) of the antibody solution to a phosphate buffered saline solution (diluting 1:1100) containing casein (0.5 weight %) as a blocking protein and Lonzaine ® C amphoteric surfactant (0.01 weight %), then filtered through a 0.22 μmeter filter to obtain a working solution.

The labeled polyclonal antibody used was a goat anti-mouse IgG antibody conjugated to horseradish peroxidase (obtained from Bio-Rad Laboratories). This conjugate was diluted to about 1:2000 in a phosphate buffered saline solution containing casein (0.5 weight %) and Lonzaine ® C amphoteric surfactant (0.01 weight %), then filtered through a 0.22 μm filter to obtain a working solution.

EXAMPLE 1: Extraction Composition

An antigen extraction solution was prepared from the following components: sodium azide (0.027 molar), sodium chloride (0.27 molar), ethanolamine hydrochloride (0.47 molar), disodium ethylenediaminetetraacetic acid (0.045 molar), Emcol ® CC-36 cationic surfactant (quaternary ammonium chlorides of polypropoxy-t-amines, available from Witco Chemical, 0.45 weight percent from a 10% solution in methanol) and sodium hydroxide (0.66 molar, pH 11)

EXAMPLE 2: Determination of Chlamydia trachomatis Antigen Using Extraction Composition This example demonstrates the practice of the present invention to extract *C. trachomatis* lipopolysaccharide and major outer membrane protein antigens.

Elementary body protein (25,000 pg protein in 81.5 μl of bovine serum albumin/phosphate buffered saline) was added to an extraction composition (1418.5 μl) of the present invention, and mixed and held at room temperature for about 5 minutes. Two corresponding extraction solutions were prepared without antigen.

Hydrogen peroxide solution (8 weight %, 1500 μl) was added to each extraction solution to remove endogenous catalase, peroxidase and myeloperoxidase. The resulting mixtures were again held at room temperature for 5 minutes.

A portion of each extraction solution (120 μl) was added to the wells of an individual disposable test device designed similar to that described in copending and commonly assigned U.S. Ser. No. 19,810 (noted above), and fluids were allowed to drain through. The device contained a 5 μm microporous membrane having quaternary ammonium groups on the surface thereof commercially available as the Pall Biodyne ®-B membrane (Pall Corp.). Prior to use, the membrane was treated with Zonyl ™ FSN (a nonionic fluorinated surfactant available from DuPont).

Portions (120 μl) of each of the anti-LPS and anti-MOMP solutions (described above), and a portion (120 μl) of both antibody solutions combined were added to each well of the test device while fluid was allowed to flow through. Incubation was carried out at room temperature for about 5 minutes. Following incubation, the resulting antigen-antibody complex was washed twice with a solution (160 μl) of Emcol ® CC-9 cationic surfactant (0.75 weight %) in phosphate buffered saline solution (pH 7.2).

A solution (120 μl) of the goat anti-mouse antibodies labeled with peroxidase was added to each well and allowed to flow through the membrane upon contact. Incubation at room temperature was carried out again for 5 minutes to form an antigen-antibody-labeled antibody complex ionically bound to the membrane.

After washing twice with the wash solution described above, a dye-providing composition was added to each test well. This composition included hydrogen peroxide (10 mmolar), 2-(4-hydroxy-3-methoxyphenyl)-4,5-bis(4-methoxyphenyl)imidazole leuco dye (0.005 weight %), poly(vinyl pyrrolidone) (1 weight %), 4'-hydroxyacetanilide (5 mmolar) and diethylene triaminepentaacetic acid (10 mmolar).

Within about 10 minutes, a red dye was observed in the test well indicating the presence of chlamydial antigen obtained from the specimen. The transmission densities were measured and the results are provided in Table I below as the difference ($\Delta D_T$) between extraction solutions with antigen and those without antigen. They indicate that the extraction composition of this invention was effective in extracting both antigens from the chlamydial organisms, and particularly effective in extracting the major outer membrane protein antigen.

TABLE I

| Antigen | $\Delta T$ for Extraction Compositions |
|---|---|
| LPS Alone | 0.085 |
| MOMP Alone | 0.179 |
| LPS + MOMP | 0.165 |

EXAMPLE 3: Effect of pH on Chlamydial Antigen Extraction

Serovar K elementary bodies were obtained from Professor J. Newhall (Indiana University) and working solutions were prepared as follows:

Solution B (18 μl) from above was mixed with extraction solution (1982 μl) to make a test solution containing 5000 pg antigen/120 μl.

Solution B (9 μl) and extraction solution (1991 μl) were mixed to prepare a test solution containing 2500 pg antigen/120 μl.

Solution C (36 μl) and extraction solution (1964 μl) were mixed to prepared a test solution containing 1000 pg antigen/120 μl.

A Control solution containing extraction solution (2000 μl) without antigen was also prepared.

Mouse anti-LPS monoclonal antibody composition was prepared having antibody solution (10 μl), casein (0.5 weight %) and Lonzaine ® C surfactant (0.01 weight % in 14.99 μl).

Anti-mouse monoclonal antibody conjugated to horseradish peroxidase was included in a composition (100 μl), casein (0.5 weight %) and Lonzaine ® C surfactant (0.01 weight % in 9.9 μl).

Serovar K elementary bodies were extracted at different pH values (9.5, 10.25 and 11.0). The extracted antigen was used in assays carried out as described in Example 1, and the resulting transmission densities are shown in Table II below. The data indicate that extraction at pH 11 using an alcoholamine provided the best sensitivity with low background.

TABLE II

| Antigen | $D_T$ at Extraction pH | | |
|---|---|---|---|
| Concentration (pg) | 9.5 | 10.25 | 11.0 |
| 5000 | 0.062 | 0.078 | 0.095 |
| 2500 | 0.042 | 0.068 | 0.070 |
| 1000 | 0.018 | 0.040 | 0.040 |
| Control (0) | 0.010 | 0.022 | 0.015 |

EXAMPLE 4: Assay for Chlamydial Antigen Using a Labeled Chlamydial Antibody

This example illustrates an assay for *C. trachomatis* using a labeled chlamydial antibody. Two different antibodies directed to the major outer membrane protein were conjugated to horseradish peroxidase by a known method (Yoshitake, *Eur. J. Biochem.*, 101, 395, 1979). The conjugates were kept in phosphate buffered saline solution (pH 7.4) containing 0.01% (by weight) thimerosal until used in the assay.

Serovar H elementary bodies were obtained as described above. Antigen solution B (identified above, 24.5 μl) was mixed with the extraction composition of Example 1 (1475.5 μl) for 5 minutes at room temperature to provide a first extract solution (1500 μl) containing $1.13 \times 10^5$ pg antigen (this results in a final antigen concentration in the assay of about 4500 pg/120 μl test sample). A second extract solution was prepared by appropriate dilution of the first extract solution to provide a final antigen concentration in the assay of 1500 pg/120 μl test sample.

Hydrogen peroxide (1.5 ml of 8% solution) was added to each antigen extract solution identified above, mixed and kept at room temperature for 5 minutes.

The solutions (120 μl) were then added to disposable test devices containing Biodyne ® nylon microporous membrane which had been precoated with Zonyl ™ FSN surfactant (0.05%, by weight), and allowed to flow through.

The peroxidase-labeled antibodies were added in combination (120 μl) with casein and Lonzaine ® amphoteric surfactant as follows: conjugate 1 was added with 1.25% (by weight) casein and 0.025% (by weight) surfactant, and conjugate 2 was added with 2% (by weight) casein and 0.04% (by weight) surfactant. Incubation for 5 minutes at room temperature followed.

The membranes were then washed twice with a solution of Emcol ® CC-9 cationic surfactant (0.75 weight %, 160 μl) in phosphate buffered saline solution.

Leuco dye solution (120 μl) was added to the test devices, incubation followed for 10 minutes at room temperature and the dye density was determined.

A Control solution containing no antigen was similarly tested to indicate background density.

The results are shown in Table III below as the difference in transmission density ($\Delta D_T$) between the test solution and the Control solution.

TABLE III

| Final Antigen | $\Delta D_T$ | |
|---|---|---|
| Concentration (pg) | Antibody Conjugate 1 | Antibody Conjugate 2 |
| 1500 | 0.094 | 0.081 |
| 4500 | 0.194 | 0.182 |

The invention has been described in detail with particular reference to preferred embodiments thereof, but it will be understood that variations and modifications can be effected within the spirit and scope of the invention.

We claim:

1. A method for extracting antigen from chlamydial, gonococcal or herpes organisms consisting essentialy of:
   A. providing a specimen suspected of containing chlamydial, gonococcal or herpes organisms, and
   B. contacting said specimen with an extraction composition which has a pH of at least about 9 and comprises a strong base and an alcoholamine or salt thereof present in an amount of at least about 1 mg/ml to extract chlamydial, gonococcal or herpes antigen, respectively, for detection, said contacting being carried out at a temperature of less than about 40° C.

2. The method of claim 1 wherein said extraction composition has a pH of at least about 10.

3. The method of claim 1 for the extraction of a chlamydial antigen.

4. A method for the determination of a chlamydial, gonococcal or herpes organism, comprising:
   A. extracting chlamydial, gonococcal or herpes antigen from a specimen suspected of containing chlamydial, gonococcal or herpes organisms, respectively,
   extraction consisting essentially of contacting said specimen with an extraction composition having a pH of at least about 9 and comprising a strong base and an alcoholamine or salt thereof present in an amount of at least about 1 mg/ml, said extraction being carried out at a temperature of less than about 40° C. to provide a test solution,
   B. without changing the pH of said test solution, contacting said extracted antigen with chlamydial, gonococcal or herpes antibodies, respectively, to form an immunological complex, and
   C. determining the presence of said complex as an indication of the presence of chlamydial, gonococcal or herpes organisms, respectively, in said specimen.

5. The method of claim 4 wherein said antibodies are labeled for detection.

6. The method of claim 4 wherein said antibodies are unlabeled and said antibody-antigen complex is determined using an anti-antibody which is labeled for detection.

7. The method of claim 4 for the determination of chlamydial organisms.

8. The method of claim 4 for the determination of gonococcal organisms.

9. The method of claim 4 for the determination of herpes viruses.

10. The method of claim 4 wherein said extraction composition further comprises either a reducing agent, a cationic surfactant or both.

* * * * *